United States Patent
Kaemmerer et al.

(10) Patent No.: US 11,628,302 B2
(45) Date of Patent: *Apr. 18, 2023

(54) CLOSED-LOOP STIMULATION THERAPY IN EVENT OF LOSS OF SENSOR DATA

(71) Applicant: Medtronic, Inc., Minneapolis, MN (US)

(72) Inventors: William F. Kaemmerer, Edina, MN (US); Duane L. Bourget, Andover, MN (US); Timothy J. Denison, Oxford (GB); Eric J. Panken, Edina, MN (US); Scott R. Stanslaski, Shoreview, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 323 days.

This patent is subject to a terminal disclaimer.

(21) Appl. No.: 17/017,442

(22) Filed: Sep. 10, 2020

(65) Prior Publication Data
US 2020/0406040 A1 Dec. 31, 2020

Related U.S. Application Data

(63) Continuation of application No. 15/666,986, filed on Aug. 2, 2017, now Pat. No. 10,799,700.

(51) Int. Cl.
*A61N 1/36* (2006.01)
*A61N 1/05* (2006.01)
*A61N 1/372* (2006.01)

(52) U.S. Cl.
CPC ....... *A61N 1/36139* (2013.01); *A61N 1/0534* (2013.01); *A61N 1/3606* (2013.01); *A61N 1/37247* (2013.01); *A61N 1/36142* (2013.01)

(58) Field of Classification Search
CPC .............. A61B 5/0482; A61N 1/36135; A61N 1/36067; A61N 1/36139
See application file for complete search history.

(56) References Cited

U.S. PATENT DOCUMENTS

| | | |
|---|---|---|
| 6,731,978 B2 | 5/2004 | Olson et al. |
| 6,768,920 B2 | 7/2004 | Lange et al. |
| 10,799,700 B2 * | 10/2020 | Kaemmerer ....... A61N 1/37247 |
| 2005/0049656 A1 | 3/2005 | Peterson et al. |
| 2005/0209644 A1 | 9/2005 | Heruth et al. |
| 2008/0269812 A1 | 10/2008 | Gerber et al. |
| 2008/0269843 A1 | 10/2008 | Gerber et al. |

(Continued)

OTHER PUBLICATIONS

International Search Report and Written Opinion of International Application No. PCT/US2018/037691, dated Sep. 14, 2018, 11 pp.

(Continued)

*Primary Examiner* — Jon Eric C Morales
(74) *Attorney, Agent, or Firm* — Shumaker & Sieffert, P.A.

(57) ABSTRACT

A medical device may receive sensor data from sensing sources, and determine confidence levels for sensor data received from each of the plurality of sensing sources. Each of the confidence levels of the sensor data from each of the sensing sources is a measure of accuracy of the sensor data received from respective sensing sources. The medical device may also determine one or more therapy parameter values based on the determined confidence levels, and cause delivery of therapy based on the determined one or more therapy parameter values.

26 Claims, 5 Drawing Sheets

(56) References Cited

U.S. PATENT DOCUMENTS

| | | |
|---|---|---|
| 2011/0251505 A1 | 10/2011 | Narayan et al. |
| 2013/0079656 A1 | 3/2013 | Dripps et al. |
| 2014/0213926 A1 | 7/2014 | Vaidyanathan |
| 2019/0038902 A1 | 2/2019 | Kaemmerer et al. |

OTHER PUBLICATIONS

Prosecution History from U.S. Appl. No. 15/666,986, dated Dec. 26, 2019 through Jun. 4, 2020 49 pp.

International Preliminary Report on Patentability from International Application No. PCT/US2018/037691, dated Feb. 4, 2020, 7 pp.

First Office Action and Search Report, and translation thereof, from counterpart Chinese Application No. 201880048967.3 dated Dec. 29, 2022, 13 pp.

* cited by examiner

| RULES | CONTROL POLICIES | | | |
|---|---|---|---|---|
| CONFIDENCE LEVEL OF SENSOR DATA FROM ALL SENSING SOURCES > 80% | A1 | B1 | C1 | D1 |
| | A2 | B2 | C2 | D2 |
| | A3 | B3 | C3 | D3 |
| | A4 | B4 | C4 | D4 |
| CONFIDENCE LEVEL OF SENSOR DATA FROM FIRST AND SECOND SENSING SOURCES > 80%, CONFIDENCE LEVEL FROM THIRD SENSING SOURCE < 80% | A1 | B1 | C1 | |
| | A2 | B2 | C2 | |
| | A3 | B3 | | |
| ⋮ | | | | |
| CONFIDENCE LEVEL OF SENSOR DATA FROM ALL SENSING SOURCES < 20% | A1 | B1 | | |
| | A2 | | | |

FIG. 3

CLOSED-LOOP STIMULATION THERAPY IN EVENT OF LOSS OF SENSOR DATA

This application is a continuation of U.S. patent application Ser. No. 15/666,986, filed Aug. 2, 2017, the entire contents of which are incorporated herein by reference.

TECHNICAL FIELD

The disclosure relates to therapy delivery by a medical device.

BACKGROUND

Medical devices, such as electrical stimulators or therapeutic agent delivery devices, may be used in different therapeutic applications, such as deep brain stimulation (DBS), spinal cord stimulation (SCS), pelvic stimulation, gastric stimulation, peripheral nerve stimulation, functional electrical stimulation or delivery of pharmaceutical agent, insulin, pain relieving agent or anti-inflammatory agent to a target tissue site within a patient. A medical device may be configured to deliver therapy to a patient to treat a variety of symptoms or patient conditions such as chronic pain, tremor, Parkinson's disease, other types of movement disorders, seizure disorders (e.g., epilepsy), urinary or fecal incontinence, sexual dysfunction, obesity, mood disorders, gastroparesis or diabetes.

In some therapy systems, an electrical stimulator, which may be implantable in some instances, delivers electrical therapy to a target tissue site within a patient with the aid of one or more electrodes, which may be deployed by medical leads, on a housing of the electrical stimulator, or both. In addition to or instead of electrical stimulation therapy, a medical device, which may be implantable in some instances, may deliver a therapeutic agent to a target tissue site within a patient with the aid of one or more fluid delivery elements, such as a catheter or a therapeutic agent eluting patch.

SUMMARY

The disclosure describes example systems, devices, and methods for therapy adjustment in response to loss of sensor data, where loss of sensor data includes full or partial dropout of sensor data. In autonomous adaptive therapy systems, sensed data is used to adapt the therapy in real time. However, there may be a reduction in confidence of the accuracy of the sensor data due to full or partial dropout of sensor data. With sensor data having reduced accuracy, there may be a possibility that a medical device selects therapy program/parameters that otherwise should not have been selected because the device relied on sensor data that was not accurate. In the examples described in this disclosure, a medical device may evaluate a set of rules to determine which sets of therapy programs/parameters are available for therapy delivery. The set of rules may be based upon the confidence in the accuracy of sensor data, where complete loss of sensor data results in zero confidence in accuracy of sensor data, and partial loss of sensor data results in non-zero degrees of confidence in accuracy of sensor data.

In one example, the disclosure describes a method of therapy delivery, the method comprising receiving sensor data generated by plurality of hardware sensing sources, determining confidence levels for sensor data generated by each of the plurality of sensing sources, wherein each of the confidence levels of the sensor data from each of the sensing sources is a measure of accuracy of the sensor data received from respective sensing sources, determining one or more therapy parameter values based on the determined confidence levels, and causing delivery of therapy based on the determined one or more therapy parameter values.

In one example, the disclosure describes a medical system for therapy delivery, the medical system comprising a plurality of hardware sensing sources configured to generate sensor data, and a processing circuit. The processing circuit is configured to receive the sensor data generated by the plurality of hardware sensing sources, determine confidence levels for sensor data generated by each of the plurality of sensing sources, wherein each of the confidence levels of the sensor data from each of the sensing sources is a measure of accuracy of the sensor data received from respective sensing sources, determine one or more therapy parameter values based on the determined confidence levels, and cause delivery of therapy based on the determined one or more therapy parameter values.

In one example, the disclosure describes a medical device for therapy delivery, the medical device comprising means for receiving sensor data generated by plurality of hardware sensing sources, means for determining confidence levels for sensor data generated by each of the plurality of sensing sources, wherein each of the confidence levels of the sensor data from each of the sensing sources is a measure of accuracy of the sensor data received from respective sensing sources, means for determining one or more therapy parameter values based on the determined confidence levels, and means for causing delivery of therapy based on the determined one or more therapy parameter values.

In one example, the disclosure describes a computer-readable storage medium having instructions stored thereon that when executed cause a processing circuit of a medical device for therapy delivery to receive sensor data generated by plurality of hardware sensing sources, determine confidence levels for sensor data generated by each of the plurality of sensing sources, wherein each of the confidence levels of the sensor data from each of the sensing sources is a measure of accuracy of the sensor data received from respective sensing sources, determine one or more therapy parameter values based on the determined confidence levels, and cause delivery of therapy based on the determined one or more therapy parameter values.

The details of one or more examples are set forth in the accompanying drawings and the description below. Other features, objects, and advantages will be apparent from the description and drawings, and from the claims.

BRIEF DESCRIPTION OF DRAWINGS

FIG. 3 is a conceptual diagram illustrating a hierarchy of therapy programs defining operation of the medical device of FIG. 2 and associated rules for determining availability of the therapy programs.

DETAILED DESCRIPTION

Figure 1:
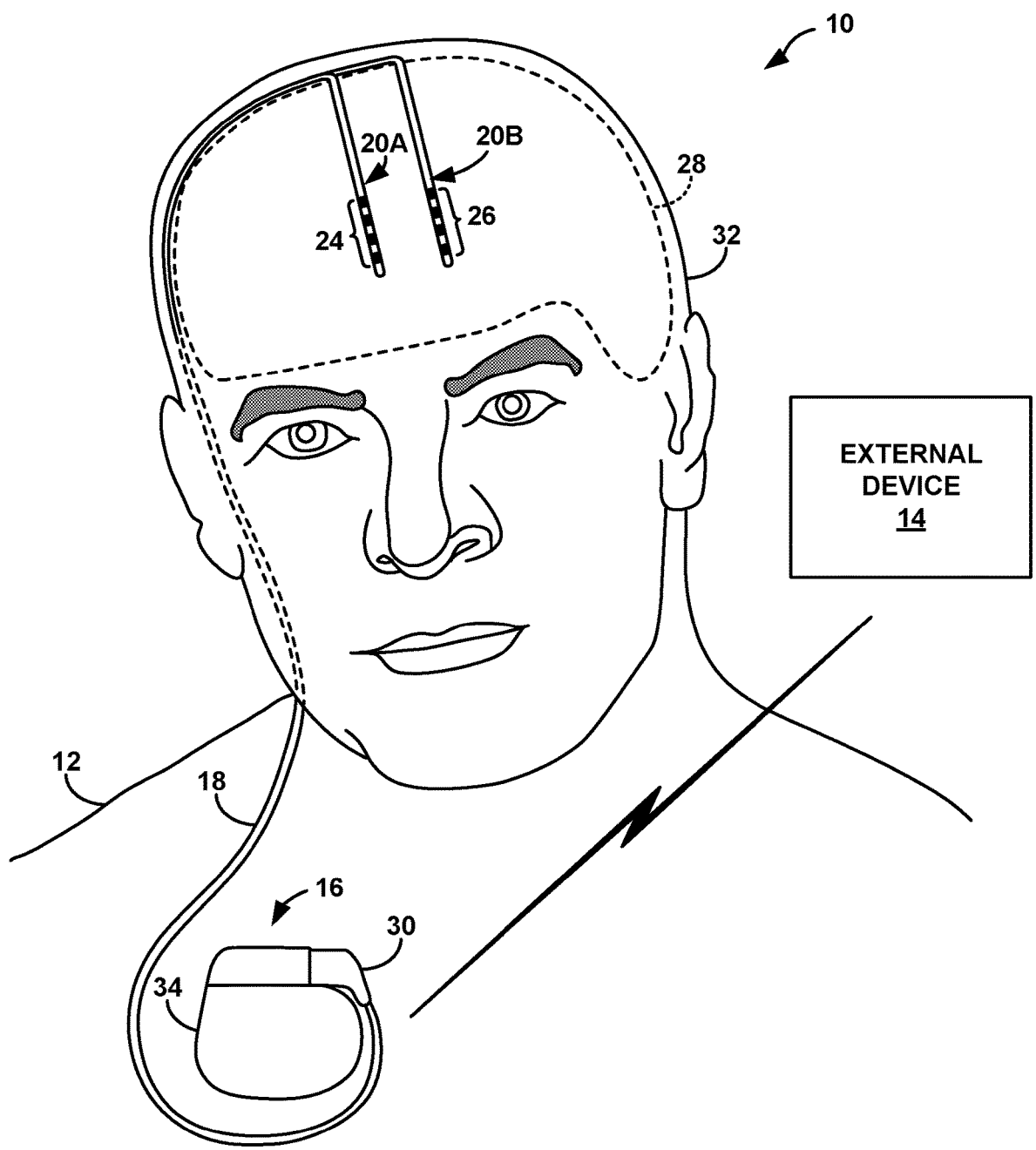
FIG. 1 is a conceptual diagram illustrating an example deep brain stimulation (DBS) system configured to sense a bioelectrical brain signal and deliver electrical stimulation therapy to a tissue site within a brain of a patient.

The disclosure describes example systems, devices, and methods for therapy delivery in the event of loss of sensor data from one or more sensing sources. In a closed-loop therapy system, a medical device (e.g., implantable medical device or external device) receives sensor data from one or more sensing sources (e.g., hardware sensing sources such as sensors, sensing circuitry, accelerometers, etc.), and determines therapy parameter values (e.g., amplitude, frequency, pulse width, etc. in the case of electrical stimulation) based on the sensor data. However, it may be possible for there to be loss of sensor data from various causes such as break in a lead, wearing out of an accelerometer, electrical interference causing loss of communication between an external sensor and the medical device, and the like.

Loss of sensor data is used to generally describe conditions where the data generated by a sensor may be unavailable or may not be accurate. One example of loss of sensor data may be full dropout of sensor data, where no sensor data is being received from a sensor. Another example of loss of sensor data may be intermittent or partial dropout of sensor data, where a portion of the sensor data is not received from the sensor. Another example of loss of sensor data may be reception of sensor data that is outside of a valid range or band. For instance, there may be a maximum possible value and a minimum possible value for the sensor data (e.g., based on what is being sensed), and loss of sensor data may include the case where the sensor data is greater than the maximum possible value or less than the minimum possible value (e.g., outside of the valid band). Other examples of loss of sensor data are possible including various examples where the received sensor data may not be accurate.

Because the medical device may utilize the sensor data for therapy parameter determination (e.g., setting or adjustment), the medical device may determine less effective therapy parameter values when the received sensor data is not accurate as compared to when the received sensor data is accurate. To minimize selection of less effective therapy parameter values, this disclosure describes example techniques for therapy parameter determination when there is loss of sensor data. As one example, this disclosure describes a hierarchical arrangement of control policies associated with a set of rules. A control policy identifies a set of therapy parameter values that may be available for determining the therapy parameter values of the therapy that is to be delivered. Each rule identifies a plurality of conditions. As an example, the plurality of conditions may be conditions related to the accuracy of the sensor data.

In general, a control policy may be considered as a method to select therapy parameter values based on the system's estimated state and the system's transfer function. The control policy may determine the set of parameters based on the current state of the system. For instance, a control policy may determine the values of the therapy parameter values based on the current system state.

If the medical device determines that the plurality of conditions of a first rule are satisfied, then the medical device may determine therapy parameter values from the control policies associated with the first rule. If, however, the medical device determines that the plurality of conditions of the first rule are not satisfied, then the medical device may determine whether the conditions of a second rule are satisfied, and so forth. If the plurality of conditions is not satisfied for any of the rules, then the medical device may determine therapy parameter values from a default set of control policies that define a default set of therapy parameter values.

In some examples, the medical device may evaluate confidence levels of the sensor data against the conditions of the rules. A confidence level is a measure of accuracy of sensor data received from respective sensing sources. For example, a high confidence value is indicative of high accuracy of the sensor data meaning that the sensors are operating correctly. A low, including zero, confidence value is indicative of low accuracy of the sensor data meaning that the sensors are not operating correctly or there is dropout in the sensor data or errors in the reception of the sensor data from the sensors, other reasons are also possible. There may be various ways in which the medical device may determine the confidence level of the sensor data. As one example, the medical device may perform data pre-processing on the received sensor data and determine how many samples are missing or outside of a valid band. The confidence level may be inversely proportional to the number of samples (e.g., sensor data values) in the sensor data that are missing or outside the valid band (e.g., the more missing or out-of-band samples, the lower the confidence level).

The conditions of the rules may be based on comparisons to confidence level thresholds. For instance, the conditions for the first rule may be that the confidence level for the sensor data from all sensing sources should be greater than a particular confidence level threshold, the conditions for the second rule may be that the confidence level for sensor data from all but one sensing source should be greater than a first confidence level, a second confidence level, and so forth. Based on the confidence level, the medical device may be configured to determine therapy parameter values (e.g., by determining therapy parameter values from the control policies associated with the rule for which the confidence levels are compliant with all conditions of that rule).

In some examples, the missing or out-of-band samples may cause the medical device to adjust therapy parameter values. As one example, if an expected sample is missing, the medical device may determine that the amplitude of the therapy is insufficient, and unnecessarily increase amplitude.

The medical device may be configured to replace the missing or out-of-band samples, which may result in reduction of unnecessary therapy adjustment. One example way in which the medical device may replace missing or out-of-band samples is to interpolate values based on valid samples. As an example, the medical device may utilize linear interpolation with one or more preceding samples to the missing or out-of-band samples and with one or more subsequent samples to the missing or out-of-band samples to generate interpolated sample values that replace (e.g., fill-in) the missing or out-of-band sample values. For instance, the medical device may interpolate sensor data values in error locations (e.g., missing or out-of-band samples) based on sensor data values in non-error locations of the sensor data.

One example way to determine the confidence levels may be based on the interpolation. For example, the number of samples for which interpolation is performed may be inversely correlated to the confidence levels (e.g., the more samples that need to be filled in with interpolation, the lower the confidence level). If greater than a threshold number of samples need to be interpolated (e.g., if there are greater than a threshold number of interpolated sensor data values), then the medical device may drop down to the default set of control policies.

FIG. 1 is a conceptual diagram illustrating an example therapy system 10 that is configured to deliver therapy to patient 12 to manage a disorder of patient 12. In some examples, therapy system 10 may deliver therapy to patient 12 to manage a movement disorder or a neurodegenerative impairment of patient 12. Patient 12 ordinarily will be a human patient. In some cases, however, therapy system 10 may be applied to other mammalian or non-mammalian non-human patients. A movement disorder may be characterized by one or more symptoms, such as, but not limited to, impaired muscle control, motion impairment or other movement problems, such as rigidity, bradykinesia, rhythmic hyperkinesia, non-rhythmic hyperkinesia, dystonia, tremor, and akinesia. In some cases, the movement disorder may be a symptom of Parkinson's disease or Huntington's disease. However, the movement disorder may be attributable to other patient conditions.

As additional examples, therapy system 10 may be configured to deliver therapy to manage other patient conditions, such as, but not limited to, seizure disorders (e.g., epilepsy), psychiatric disorders, behavior disorders, mood disorders, memory disorders, mentation disorders, Alzheimer's disease, or other neurological or psychiatric impairments, in addition to or instead of a movement disorder. Examples of psychiatric disorders include major depressive disorder (MDD), bipolar disorder, anxiety disorders, post traumatic stress disorder, dysthymic disorder, and obsessive compulsive disorder (OCD). Treatment of other patient disorders via delivery of therapy to brain 28 or another suitable target therapy delivery site in patient 12 are also contemplated.

In the example shown in FIG. 1, therapy system 10 includes medical device programmer 14, implantable medical device (IMD) 16, lead extension 18, and one or more leads 20A and 20B (collectively "leads 20") with respective sets of electrodes 24, 26. IMD 16 includes a therapy module that includes a stimulation generator that is configured to generate and deliver electrical stimulation therapy to one or more regions of brain 28 of patient 12 via a subset of electrodes 24, 26 of leads 20A and 20B, respectively. In the example shown in FIG. 1, therapy system 10 may be referred to as a deep brain stimulation (DBS) system because IMD 16 provides electrical stimulation therapy directly to tissue within brain 28, e.g., a tissue site under the dura mater of brain 28 or one or more branches or nodes, or a confluence of fiber tracks. In other examples, leads 20 may be positioned to deliver therapy to a surface of brain 28 (e.g., the cortical surface of brain 28). In some examples, IMD 16 may provide cortical stimulation therapy to patient 12, e.g., by delivering electrical stimulation to one or more tissue sites in the cortex of brain 28. In some examples, IMD 16 may provide vagal nerve stimulation (VNS) therapy to patient 12 by delivering electrical stimulation to one or more vagal nerve tissue sites.

In still other examples, IMD 16 may provide spinal cord stimulation (SCS), pelvic stimulation, gastric stimulation, peripheral nerve stimulation, functional electrical stimulation or delivery of a pharmaceutical agent, insulin, pain relieving agent or anti-inflammatory agent to a target tissue site within a patient. Thus, although electrical stimulation therapy is primarily referred to throughout the remainder of the application, in other examples, therapy system 10 may be configured to deliver other types of therapy in addition to or instead of electrical stimulation therapy.

In the example shown in FIG. 1, IMD 16 may be implanted within a subcutaneous pocket in the pectoral region of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. IMD 16 can be constructed of a biocompatible material that resists corrosion and degradation from bodily fluids. IMD 16 may comprise a hermetic housing 34 to substantially enclose components, such as a processor, therapy module, and memory.

In the example shown in FIG. 1, leads 20 are implanted within the right and left hemispheres, respectively, of brain 28 in order to deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere at multiple target tissue sites or IMD 16 may be coupled to a single lead that is implanted in one or both hemispheres of brain 28.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. Different neurological or psychiatric disorders may be associated with activity in one or more of regions of brain 28, which may differ between patients. For example, a suitable target therapy delivery site within brain 28 for controlling a movement disorder of patient 12 may include one or more of the pedunculopontine nucleus (PPN), thalamus, basal ganglia structures (e.g., globus pallidus, substantia nigra or subthalamic nucleus), zona inserta, fiber tracts, lenticular fasciculus (and branches thereof), ansa lenticularis, and/or the Field of Forel (thalamic fasciculus). The PPN may also be referred to as the pedunculopontine tegmental nucleus.

As another example, in the case of MIDD, bipolar disorder, OCD, or other anxiety disorders, leads 20 may be implanted to deliver electrical stimulation to the anterior limb of the internal capsule of brain 28, only the ventral portion of the anterior limb of the internal capsule (also referred to as a VC/VS), the subgenual component of the cingulate cortex (which may be referred to as CG25), anterior cingulate cortex Brodmann areas 32 and 24, various parts of the prefrontal cortex, including the dorsal lateral and medial pre-frontal cortex (PFC) (e.g., Brodmann area 9), ventromedial prefrontal cortex (e.g., Brodmann area 10), the lateral and medial orbitofrontal cortex (e.g., Brodmann area 11), the medial or nucleus accumbens, thalamus, intralaminar thalamic nuclei, amygdala, hippocampus, the lateral hypothalamus, the Locus ceruleus, the dorsal raphe nucleus, ventral tegmentum, the substantia nigra, subthalamic nucleus, the inferior thalamic peduncle, the dorsal medial nucleus of the thalamus, the habenula, the bed nucleus of the stria terminalis, or any combination thereof. Target tissue sites not located in brain 28 of patient 12 are also contemplated.

As another example, in the case of a seizure disorder or Alzheimer's disease, for example, leads 20 may be implanted to deliver electrical stimulation to regions within the Circuit of Papez, such as, e.g., the anterior thalamic nucleus, the internal capsule, the cingulate, the fornix, the mammillary bodies, the mammillothalamic tract (mammillothalamic fasciculus), and/or hippocampus. For example, in the case of a seizure disorder, IMD 16 may deliver therapy to a region of brain 28 via a selected subset of electrodes 24, 26 to suppress cortical activity within the anterior thalamic nucleus, hippocampus, or other brain region associated with the occurrence of seizures (e.g., a seizure focus of brain 28). Conversely, in the case of Alzheimer's disease, IMD 16 may deliver therapy to a region of brain 28 via electrodes 24, 26 to increase cortical activity within the anterior thalamic nucleus, hippocampus, or other brain region associated with Alzheimer's disease. As another example, in the case of depression (e.g., MDD), IMD 16 may deliver therapy to a region of brain 28 via electrodes 24, 26 to increase cortical activity within one or more regions of brain 28 to effectively treat the patient disorder. As another example, IMD 16 may deliver therapy to a region of brain 28 via electrodes 24, 26 to decrease cortical activity within one or more regions of brain 28, such as, e.g., the frontal cortex, to treat the disorder.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

Leads 20 may be implanted within a desired location of brain 28 via any suitable technique, such as through respective burr holes in the skull of patient 12 or through a common burr hole in the cranium 32. Leads 20 may be placed at any location within brain 28 such that electrodes 24, 26 of leads 20 are capable of providing electrical stimulation to targeted tissue during treatment. Electrical stimulation generated from the stimulation generator (not shown) within the therapy module of IMD 16 may help mitigate the symptoms of movement disorders, such as by improving the performance of motor tasks by patient 12 that may otherwise be difficult. These tasks may include, for example, at least one of initiating movement, maintaining movement, grasping and moving objects, improving gait and balance associated with narrow turns, and the like. The exact therapy parameter values of the electrical stimulation therapy that may help mitigate symptoms of the movement disorder (or other patient condition) may be specific for the particular target stimulation site (e.g., the region of the brain) involved as well as the particular patient and patient condition.

In the examples shown in FIG. 1, electrodes 24, 26 of leads 20 are shown as ring electrodes. Ring electrodes may be relatively easy to program and are typically capable of delivering an electrical field to any tissue adjacent to leads 20. In other examples, electrodes 24, 26 of leads 20 may have different configurations. For example, electrodes 24, 26 of leads 20 may have a complex electrode array geometry that is capable of producing shaped electrical fields, including interleaved stimulation. An example of a complex electrode array geometry, may include an array of electrodes positioned at different axial positions along the length of a lead, as well as at different angular positions about the periphery, e.g., circumference, of the lead. The complex electrode array geometry may include multiple electrodes (e.g., partial ring or segmented electrodes) around the perimeter of each lead 20, in addition to, or instead of, a ring electrode. In this manner, electrical stimulation may be directed to a specific direction from leads 20 to enhance therapy efficacy and reduce possible adverse side effects from stimulating a large volume of tissue. In some examples in which multiple leads 20 are implanted in the same hemisphere surrounding a target, steered electrical stimulation can be performed between two or more electrodes.

In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In other examples, leads 20 may have shapes other than elongated cylinders as shown in FIG. 1 with active or passive tip configurations. For example, leads 20 may be paddle leads, spherical leads, bendable leads, or any other type of shape effective in treating patient 12.

IMD 16 may deliver electrical stimulation therapy to brain 28 of patient 12 according to one or more stimulation therapy programs. A stimulation therapy program may define one or more electrical stimulation parameter values for therapy generated by a therapy module of IMD 16 and delivered from IMD 16 to brain 28 of patient 12. Where IMD 16 delivers electrical stimulation in the form of electrical pulses, for example, the electrical stimulation parameters may include amplitude mode (constant current or constant voltage), pulse amplitude, pulse width, a waveform shape, etc. In addition, if different electrodes are available for delivery of stimulation, a therapy parameter of a therapy program may be further characterized by an electrode combination, which may define selected electrodes and their respective polarities.

In some examples, IMD 16 is configured to deliver electrical stimulation therapy to brain 28 of patient 12 in an open loop manner, in which IMD 16 delivers the stimulation therapy without intervention from a user or a sensor. In other examples, IMD 16 is configured to deliver electrical stimulation therapy to brain 28 of patient 12 in a closed loop manner, in which IMD 16 controls the timing of the delivery of electrical stimulation to brain 28, the output parameters of the electrical stimulation, or both based on one or more of user input and input from one or more sensing sources. The sensing sources may, for example, provide feedback that may be used to control the electrical stimulation output from IMD 16. For instance, therapy system 10 is an example of an autonomous adaptive system that delivers therapy to patient 12 in a manner that varies in real time according to sense information about patient 12.

For example, the sensor data received from sensing sources forms feedback that is used to control the therapy parameter values. As an example, if IMD 16 determines that the amplitude of the sensed signal is greater than expected (e.g., patient 12 is experiencing too many tremors), IMD 16 may adjust one or more of the amplitude, pulse width, frequency, etc. of the therapy to reduce the amplitude of the sensed signal. In some examples, IMD 16 may adjust one or more therapy parameter values to increase the amplitude of the sensed signals, such as in examples where an increase in amplitude of a sensed signal is indicative of efficacy of therapy.

In addition to being configured to deliver therapy to manage a disorder of patient 12, therapy system 10 is configured to sense bioelectrical signals of patient 12 (e.g., bioelectrical brain signals in the example of FIG. 1), as well as other signals. It should be understood that the sensing of bioelectrical signals is not necessary in all examples. For example, for motion disorders, the signals may be generated from an accelerometer or some other device, and not necessarily from a bioelectrical signal. In general, the techniques described in this disclosure are applicable to examples where the patient generates a patient signal indicative of a patient condition that is measured by one or more hardware sensing sources. The examples of the hardware sensing sources include sensing circuitry of IMD 16, an accelerometer within IMD 16, an accelerometer worn externally by patient 12, electrodes coupled externally to patient 12, and various other such devices that sense information indicative of a patient condition.

In some examples, IMD 16 may include a sensing module that is configured to sense bioelectrical signals within one or more regions of brain 28 via a subset of electrodes 24, 26, another set of electrodes, or both. Accordingly, in some examples, electrodes 24, 26 may be used to deliver electrical stimulation from the therapy module to target sites within brain 28 as well as sense brain signals within brain 28. However, IMD 16 can also use a separate set of sensing electrodes to sense the bioelectrical brain signals. In the example shown in FIG. 1, the signals generated by electrodes 24, 26 are conducted to the sensing circuitry within IMD 16 via conductors within the respective lead 20A, 20B. In some examples, the sensing circuitry of IMD 16 may sense bioelectrical signals via one or more of the electrodes 24, 26 that are also used to deliver electrical stimulation to brain 28. In other examples, one or more of electrodes 24, 26 may be used to sense bioelectrical signals while one or more different electrodes 24, 26 may be used to deliver electrical stimulation.

Depending on the particular stimulation electrodes and sense electrodes used by IMD 16, IMD 16 may monitor bioelectrical signals and deliver electrical stimulation at the same region of brain 28 or at different regions of brain 28. In some examples, the electrodes used to sense bioelectrical signals may be located on the same lead used to deliver electrical stimulation, while in other examples the electrodes used to sense bioelectrical signals may be located on a different lead than the electrodes used to deliver electrical stimulation. In some examples, a bioelectrical signal of patient 12 may be monitored with external electrodes, e.g., scalp electrodes. Moreover, in some examples, the sensing circuitry that senses bioelectrical signals of brain 28 (e.g., the sensing circuitry that generates an electrical signal indicative of the activity within brain 28) is in a physically separate housing from outer housing 34 of IMD 16. However, in the example shown in FIG. 1 and the example primarily referred to herein for ease of description, the sensing circuitry and therapy generation circuitry of IMD 16 are enclosed within a common outer housing 34.

The bioelectrical signals sensed by IMD 16 may reflect changes in electrical current produced by the sum of electrical potential differences across brain tissue. Example bioelectrical brain signals include, but are not limited to, an electroencephalogram (EEG) signal, an electrocorticogram (ECoG) signal, a local field potential (LFP) sensed from within one or more regions of a patient's brain, a micro electrode recording (MER) and/or action potentials from single cells within the patient's brain. In some examples, LFP data can be measured ipsilaterally or contralaterally and considered as an average (e.g., a maximum or minimum or a heuristic combination thereof) or as some other value. The location at which the sensed signals are obtained may be adjusted according to a disease onset side of the body of patient 12 or severity of symptoms or disease duration. The adjustments, may, for example, be made on the basis of clinical symptoms presented and their severity, which can be augmented or annotated with recorded LFP data. A clinician or processing circuitry of IMD 16 may also add heuristic weights to ipsilaterally and/or contralaterally measured LFP data to be considered for system feedback.

In addition to bioelectrical signals from the brain, the example techniques are applicable to other types of signals such as cardiac signals, as one example. For example, seizures can sometimes be detected using both brain and cardiac (ECG) signals in conjunction, since the cardiac signals change before a seizure. In general, the techniques described in this disclosure are applicable to various signal types that are sensed using various sensor types. For instance, the techniques are applicable to sensor signals from a pressure sensor, cardiac electrogram or ECG sensor, a fluid flow sensor, an arterial venous or tissue oxygen, $CO_2$, pH (acidity) sensor, a perfusion sensor, a hemoglobin sensor, an accelerometer (single or multi-axis), a glucose sensor, a potassium or similar plasma ion sensor, a temperature sensor, and/or other sensors.

External device 14 is configured to wirelessly communicate with IMD 16 as needed to provide or retrieve therapy information. Device 14 is an external computing device that the user, e.g., the clinician and/or patient 12, may use to communicate with IMD 16. For example, device 14 may be a clinician programmer that the clinician uses to communicate with IMD 16 and program one or more therapy programs for IMD 16. In addition, or instead, device 14 may be a patient programmer that allows patient 12 to select programs and/or view and modify therapy parameter values. The clinician programmer may include more programming features than the patient programmer. In other words, more complex or sensitive tasks may only be allowed by the clinician programmer to prevent an untrained patient from making undesired changes to IMD 16. Device 14 may also be a device used to receive information from IMD 16, and may not necessarily provide functionality to program therapy.

Device 14 may be a hand-held computing device with a display viewable by the user and an interface for providing input to device 14 (i.e., a user input mechanism). For example, device 14 may include a small display screen (e.g., a liquid crystal display (LCD) or a light emitting diode (LED) display) that presents information to the user. In addition, device 14 may include a touch screen display, keypad, buttons, a peripheral pointing device or another input mechanism that allows the user to navigate through the user interface of device 14 and provide input. If device 14 includes buttons and a keypad, the buttons may be dedicated to performing a certain function, i.e., a power button, the buttons and the keypad may be soft keys that change in function depending upon the section of the user interface currently viewed by the user, or any combination thereof. Alternatively, the screen (not shown) of device 14 may be a touch screen that allows the user to provide input directly to the user interface shown on the display. The user may use a stylus or their finger to provide input to the display.

In other examples, device 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device 14. A wireless adapter coupled to the computing device may enable secure communication between the computing device and IMD 16.

When device 14 is configured for use by the clinician, device 14 may be used to transmit initial programming information to IMD 16. This initial information may include hardware information, such as the type of leads 20, the arrangement of electrodes 24, 26 on leads 20, the position of leads 20 within brain 28, initial programs defining therapy parameter values, and any other information that may be useful for programming into IMD 16. Device 14 may also be capable of completing functional tests (e.g., measuring the impedance of electrodes 24, 26 of leads 20).

The clinician may also generate and store therapy programs within IMD 16 with the aid of device 14. During a programming session, the clinician may determine one or more therapy programs that may provide efficacious therapy to patient 12 to address symptoms associated with the movement disorder (or other patient conditions). For example, the clinician may select one or more electrode combinations with which stimulation is delivered to brain 28. During the programming session, patient 12 may provide feedback to the clinician as to the efficacy of the specific program being evaluated or the clinician may evaluate the efficacy based on one or more sensed or observable physiological parameters of patient (e.g., muscle activity) or based on motion detected via one or more motion sensors that generate signals indicative of motion of patient 12. Device 14 may assist the clinician in the creation/identification of therapy programs by providing a methodical system for identifying potentially beneficial therapy parameter values.

Device 14 may also be configured for use by patient 12. When configured as a patient programmer, device 14 may have limited functionality (compared to a clinician programmer) in order to prevent patient 12 from altering critical functions of IMD 16 or taking actions that may be detrimental to patient 12.

Whether device 14 is configured for clinician or patient use, device 14 is configured to communicate with IMD 16 and, optionally, another computing device, via wireless communication. Device 14, for example, may communicate via wireless communication with IMD 16 using radio frequency (RF) telemetry techniques known in the art. Device 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Device 14 may also communicate with other programming or computing devices via exchange of removable media, such as memory cards. Further, device 14 may communicate with IMD 16 and another programmer via remote telemetry techniques known in the art, communicating via a local area network (LAN), wide area network (WAN), public switched telephone network (PSTN), or cellular telephone network, for example.

In accordance with the example techniques described in this disclosure, IMD 16 may be configured to deliver therapy to patient 12 in a closed loop manner. For instance, as noted above, IMD 16 may deliver therapy in an autonomous adaptive system in which therapy to the patient varies in real time according to sense information.

In such closed loop systems, the behavior of the system and corresponding safety for patient 12 should be controlled in the event that the sensed information, which forms the feedback from which therapy is determined, is lost or is otherwise unreliable. In such examples, IMD 16 may adjust therapy in a "graceful" manner upon loss of data, and continue to safely deliver useful therapy to patient 12.

For instance, a dropout in sensor data or out-of-band sensor data may cause IMD 16 to determine that a patient characteristic is different than the actual patient characteristic, and IMD 16 may unnecessarily adjust therapy parameter values. Avoiding the determination of therapy parameter values based on dropped or out-of-band sensor data may be insufficient to ensure that the correct therapy will be selected as there can be a reduction in confidence that the remaining sample values (e.g., in-band) in the sensor data are accurate.

In examples described in this disclosure, IMD 16 may utilize a hierarchical structure of defined control policies, where each of the control policies defines a plurality of therapy parameter values. As one example, the hierarchical structure of defined control policies may be a layered hierarchy of therapy programs, with the bottom layer including one or more "default" therapy programs that can be delivered under all circumstances.

IMD 16 may determine confidence levels for the received sensor data to determine which control policies are available, where each of the control policies defines a set of therapy parameter values and/or therapy programs that are available for therapy delivery. In general, IMD 16 may determine one or more confidence levels for sensor data received from each of the plurality of sensors, where each of the confidence levels of the sensor data from each of the sensing sources is a measure of accuracy of the sensor data received from respective sensing sources. IMD 16 may determine one or more therapy parameter values based on the determined one or more confidence levels, and one example way in which IMD 16 determines the one or more therapy parameter values is via the use of control policies.

In some examples, IMD 16 may interpolate sample values (e.g., linear interpolation, but other interpolation types are possible) for the out-of-band or missing sample values. This may allow for a reasonable value to substitute for the invalid value (e.g., out-of-band or missing sample value), and the therapy program that IMD 16 is executing may receive a stream of sensor data without invalid values, which could cause an error in the execution of the therapy program. In other words, from the perspective of the therapy program, there was no change in the sensor data. This way, changes to the therapy program to avoid the processing of invalid values may not be needed as the therapy program receives a stream of sensor data with substituted values and, as a result, without any invalid values.

There may be various ways in which IMD 16 may determine the confidence values. As one example, IMD 16 may determine a number of error locations in the received sensor data, or a number of interpolated sample values, where the error locations include invalid data (e.g., out-of-bounds or missing sample values). IMD 16 may determine the confidence level based on at least one of the determined number of error locations or the number of interpolated sample values. As another example, IMD 16 may determine a number of data packet losses (including partial packet loss) in the received sensor data. Examples of data packet loses include loss of packet that includes header information that should be available regardless of the values of the sensor data, loss of packet of communication information during configuration, and the like. IMD 16 may determine the confidence level based on the determined number of data packet losses.

As an example, if there is no invalid and/or interpolated data, then the confidence level is 100%, if 1% of the sensor data is invalid and/or interpolated, then the confidence level is 99%, and so forth. As another example, if there is greater than 80% packet loss, then the confidence level is zero. In general, the confidence level is inversely correlated to the amount of invalid and/or interpolated data. Also, in the above example, the confidence level is a percentage value; however, the example techniques are not so limited. In some examples, the confidence level may be a binary value (e.g., confidence level of one indicates data is accurate, and confidence level of zero indicates data is not accurate).

Referring back to the hierarchical structure, each of the layers may be associated with a rule (e.g., a set of conditions), where IMD 16 determines whether each of the conditions is true or false based on a comparison of the confidence levels to the conditions. If all conditions of the rule are true, then IMD 16 may select therapy parameter values from the control policies available for the layer associated with that rule. If one condition of the rule is false, then IMD 16 may determine whether each of the conditions of the rule associated with the next layer is true, and repeat these operations until IMD 16 determines a set of available control policies.

It may be possible that IMD 16 determines that the one or more confidence levels are not compliant with one or more conditions of all of the rules. In such examples, IMD 16 may determine whether conditions associated with using a set of default therapy parameter values is met. An example of the rule associated with the default therapy parameter values is an amount of time since the last change in the selected therapy parameter values (e.g., the condition is whether the therapy parameter values have changed or not changed in a certain amount of time). IMD 16 may ramp up or ramp down the therapy parameter values to the default therapy parameter values in a controlled manner so that the loss of sensor data may not lead to overly abrupt change in therapy.

Whether the conditions of the rule, associated with the default therapy parameter values, are met may not be dependent upon the sensor data. This way, the default therapy parameter values are available for selection even when there is complete loss of sensor data or complete loss in confidence of sensor data. Also, the conditions of the rule, associated with the default therapy parameter values, may be such that all conditions of the rule are met when none of the other rules are satisfied.

System 10 shown in FIG. 1 is merely one example of a therapy system that is configured to perform the techniques described in this disclosure. Systems with other configurations of leads, electrodes, and sensors are possible. For example, in other implementations, IMD 16 may be coupled to additional leads or lead segments having one or more electrodes positioned at different target tissue sites, which may be within brain 28 or outside of brain (e.g., proximate to a spinal cord of patient 12, a peripheral nerve of patient 12, a muscle of patient 12, or any other suitable therapy delivery site). The additional leads may be used for delivering different stimulation therapies to respective stimulation sites within patient 12 or for monitoring at least one physiological parameter of patient 12.

Additionally, in other examples, a system may include more than one IMD. For example, a system may include two IMDs coupled to respective one or more leads. Each IMD can deliver stimulation to a respective lateral side of patient 12 in some examples.

As another example configuration, a therapy system can include one or more leadless electrical stimulators (e.g., microstimulators having a smaller form factor than IMD 16 and may not be coupled to any separate leads). The leadless electrical stimulators can be configured to generate and deliver electrical stimulation therapy to patient 12 via one or more electrodes on an outer housing of the electrical stimulator. In examples including a plurality of leadless electrical stimulators, the leadless electrical stimulators can be implanted at different target tissue sites within patient 12. One electrical stimulator may act as a "master" module that coordinates the delivery of stimulation to patient 12 via the plurality of electrical stimulators.

In some examples, IMD 16 is not configured to deliver electrical stimulation therapy to brain of patient 12, but, rather, is only configured to sense one or more physiological parameters of patient 12, including a bioelectrical brain signal of patient 12. This type of IMD 16 may be a patient monitoring device useful for diagnosing patient 12, monitoring a patient condition 12, or to train IMD 16 or another IMD for therapy delivery.

Figure 2:
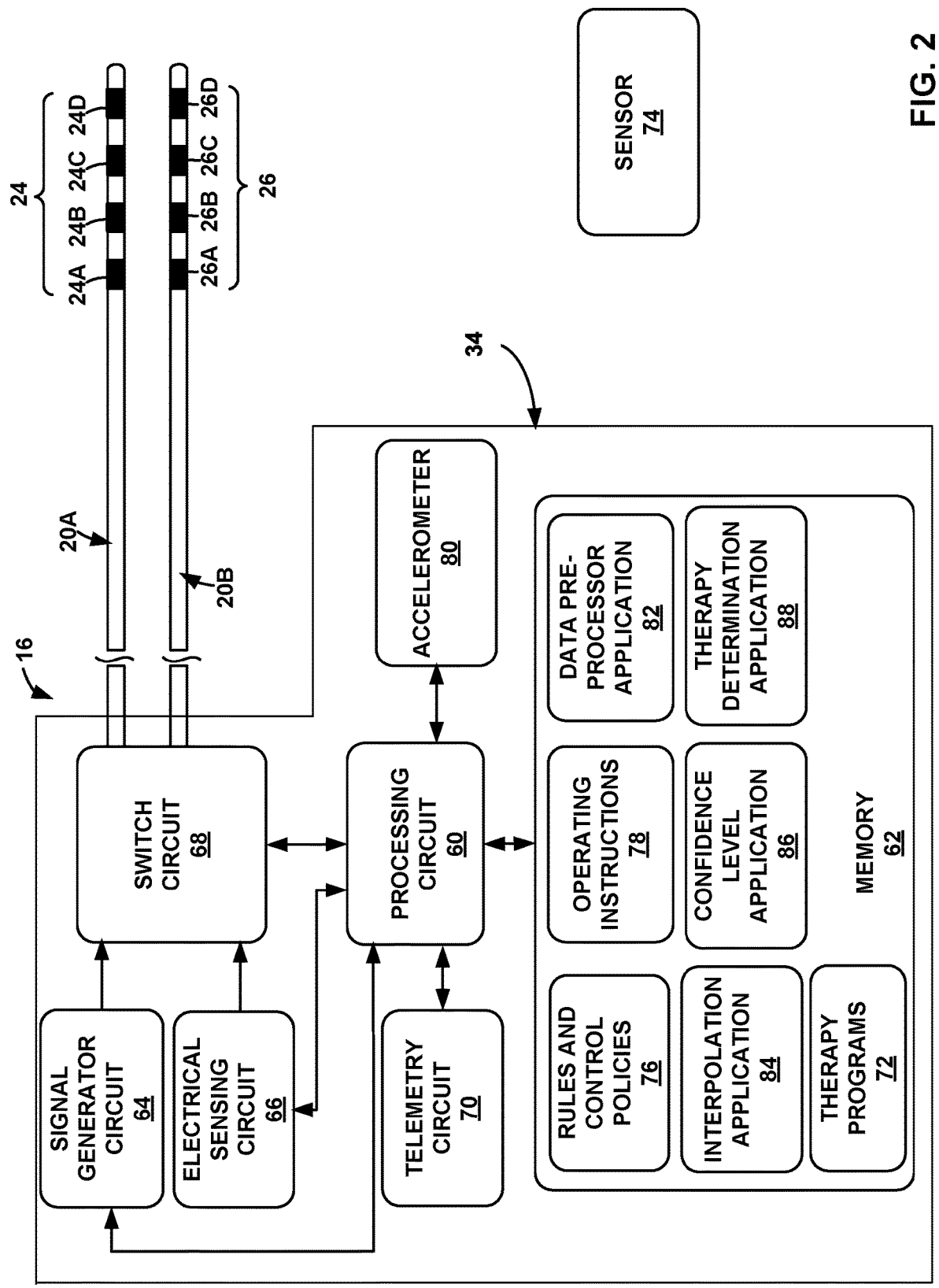
FIG. 2 is functional block diagram illustrating components of an example medical device that may form part of the system of FIG. 1.

FIG. 2 is functional block diagram illustrating components of an example IMD 16. In the example shown in FIG. 2, IMD 16 includes processing circuit 60, memory 62, signal generator circuit 64, electrical sensing circuit 66, switch circuit 68, telemetry circuit 70, and accelerometer 80. In addition, FIG. 2 illustrates sensor 74, which may be a sensing source that patient 12 wears such as on the wrist or coupled to the head. In other examples, sensor 74 could comprise one or more implantable sensors implanted at one or more locations within the patient's body that may be remote from IMD 16. For instance, sensors housed in small injectable capsules could be positioned at locations remote to IMD 16 and communicate with IMD via telemetry circuit 70 in some cases.

Memory 62, as well as other memories described herein, may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processing circuit 60, cause IMD 16 to perform various functions described herein.

In the example shown in FIG. 2, memory 62 stores therapy programs 72, rules and control policies 76, operating instructions 78, data pre-processor application 82, interpolation application 84, confidence level application 86, and therapy determination application 88. For purposes of illustration, the example techniques described in this disclosure are described with respect to processing circuit 60 executing the applications stored in memory 62, which in turn cause processing circuit 60 to perform the example techniques. However, processing circuit 60 may be hardwired to perform the example techniques described in this disclosure. Therefore, although the example techniques are described with respect to applications executed on programmable circuitry of processing circuit 60, the example techniques may be formed by fixed-function circuitry of processing circuit 60 or a combination of fixed-function and programmable circuitry of processing circuit 60.

Rules and control policies 76 store information indicative of conditions of a rule and a set of control policies associate with the rule. Therapy programs 72 define particular programs of therapy in terms of respective values for electrical stimulation parameters, such as a stimulation electrode combination, electrode polarity, current or voltage amplitude, and, if signal generator circuit 64 generates and delivers stimulation pulses, the therapy programs may define values for a pulse width and pulse rate of a stimulation signal. Rules and control policies 76 may define which ones of therapy programs 72, or which therapy parameter values more generally, are associated with which layer, and which rules are associated with which layer. Thereby, rules and control policies 76 indicate which therapy parameter values are available for selection when conditions of a particular rule are satisfied (e.g., the confidence levels are compliant with conditions of a rule).

In some examples, memory 62 may also store brain signal or other sensing data generated by sensing circuit 66 via at least one of electrodes 24, 26 and, in some cases, a reference electrode on outer housing 34 of IMD 16 or another reference electrode. In addition, in some examples, processing circuit 60 may append a time and date stamp to the brain signal data in memory 62. Operating instructions 78 guide general operation of IMD 16 under control of processing circuit 60, and may include instructions for monitoring brains signals within one or more brain regions via electrodes 24, 26 and delivering electrical stimulation therapy to patient 12. Signal generator circuit 64, under the control of processing circuit 60, generates stimulation signals for delivery to patient 12 via selected combinations of electrodes 24, 26. In some examples, signal generator circuit 64 generates and delivers stimulation signals to one or more target regions of brain 28 (FIG. 1), via a selected combination of electrodes 24, 26, based on one or more stored therapy programs 72 (or more generally therapy parameter values) that are available based on the satisfaction of conditions in rules and control policies 76. The target tissue sites within brain 28 for stimulation signals or other types of therapy may depend on the patient condition for which therapy system 10 is implemented to manage. While stimulation pulses are described, stimulation signals may be of other forms, such as continuous-time signals (e.g., sine waves) or the like.

The processing circuit described in this disclosure, including processing circuit 60, may include one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to the processing circuit described herein may be provided by a hardware device and embodied as software, firmware, hardware, or any combination thereof. Processing circuit 60 is configured to control signal generator circuit 64 according to therapy programs 72 by memory 62 to apply particular stimulation parameter values specified by one or more programs.

In the example shown in FIG. 2, the set of electrodes 24 of lead 20A includes electrodes 24A, 24B, 24C, and 24D, and the set of electrodes 26 of lead 20B includes electrodes 26A, 26B, 26C, and 26D. Processing circuit 60 may control switch circuit 68 to apply the stimulation signals generated by signal generator circuit 64 to selected combinations of electrodes 24, 26. In particular, switch circuit 68 may couple stimulation signals to selected conductors within leads 20, which, in turn, deliver the stimulation signals across selected electrodes 24, 26. Switch circuit 68 may be a switch array, switch matrix, multiplexer, or any other type of switching circuit configured to selectively couple stimulation energy to selected electrodes 24, 26 and to selectively sense bioelectrical brain signals with selected electrodes 24, 26. Hence, signal generator circuit 64 is coupled to electrodes 24, 26 via switch module 68 and conductors within leads 20. In some examples, however, IMD 16 does not include switch circuit 68.

Switch circuit 68 is illustrated as merely one example. In some examples, IMD 16 may not include switch circuit 68. Rather, IMD 16 may include a plurality of stimulation sources such as current sources that sink or source current and/or a voltage sources that output a positive or a negative voltage. In such examples, each one of electrodes 24, 26 may be coupled to separate ones of the stimulation sources. In some examples, some of electrodes 24, 26 may be coupled to the same stimulation source, and other electrodes may be coupled to another stimulation source, with the possibility that one stimulation source couples to a plurality of electrodes 24, 26. In examples where IMD 16 does not include switch circuit 68, processing circuit 60 and/or signal generator circuit 64 may selectively enable stimulation sources to deliver the stimulation.

Signal generator circuit 64 may be a single channel or multi-channel stimulation generator. In particular, signal generator circuit 64 may be capable of delivering a single stimulation pulse, multiple stimulation pulses or a continuous signal including a plurality of frequency components at a given time via a single electrode combination or multiple stimulation pulses at a given time via multiple electrode combinations. In some examples, however, signal generator circuit 64 and switch circuit 68 may be configured to deliver multiple channels on a time-interleaved basis. For example, switch circuit 68 may serve to time divide the output of signal generator circuit 64 across different electrode combinations at different times to deliver multiple programs or channels of stimulation energy to patient 12.

Sensing circuit 66, under the control of processing circuit 60, and as an example of a sensing source, is configured to sense bioelectrical signals of patient 12 via a selected subset of electrodes 24, 26 or with one or more electrodes 24, 26 and at least a portion of a conductive outer housing 34 of IMD 16, an electrode on an outer housing of IMD 16 or another reference. Processing circuit 60 may control switch circuit 68 to electrically connect sensing circuit 66 to selected electrodes 24, 26. In this way, sensing circuit 66 may selectively sense bioelectrical brain signals with different combinations of electrodes 24, 26 (and/or a reference other than an electrode 24, 26). Processing circuit 60 may monitor the efficacy of therapy delivery by IMD 16 via the sensed bioelectrical brain signals and determine whether the efficacy of therapy delivery has changed, and, in response, generate a notification (e.g., to patient 12 or patient caretaker).

Although sensing circuit 66 is incorporated into a common housing 34 with signal generator circuit 64 and processing circuit 60 in FIG. 2, in other examples, sensing circuit 66 is in a separate outer housing from outer housing 34 of IMD 16 and communicates with processing circuit 60 via wired or wireless communication techniques. In the techniques described in this disclosure, the patient signal sensed via sensing circuit 66 is one example of a patient signal indicative of a patient condition. For instance, the patient signal may be a sensed LFP signal.

Accelerometer 80 may generate a patient signal based on patient movement. As one example, accelerometer 80 may generate a patient signal having the same frequency as patient tremor. Accelerometer 80 may be utilized for purposes other than patient tremor detection. In addition, rather than or in addition to accelerometer 80, IMD 16 may include another device type such as a gyroscope that generates a patient signal based on patient movement. As another example, sensor 74 may be a gyroscope.

Also, accelerometer 80 (and possibly sensor 74) may not be necessary in every example. For instance, in examples where the techniques are for sensed patient signals such as those from sensing circuit 66, accelerometer 80 and sensor 74 may not be necessary, but may still be included. In examples where accelerometer 80 and/or sensor 74 is used, accelerometer 80 need not necessarily reside within IMD 16, and may reside elsewhere, including surgically implanted locations within patient 12. In some cases, an accelerometer may be in a small injectable housing similar to an injectable capsule for injecting at a selected location within the patient's body. Such an accelerometer 80 may communicate with IMD via telemetry circuit 70 in some instances.

Sensor 74 may communicate sensor data with processing circuit 60 via telemetry circuit 70. For example, sensor 74 may establish a communication session with processing circuit 60 via telemetry circuit 70. Part of establishing the communication session may be transferring of data packets back and forth. Once the communication session is established, sensor 74 may provide sensor data to processing circuit 60.

As illustrated, processing circuit 60 receives sensor data (e.g., the bioelectrical signal) from sensing circuit 66, which is configured to sense the bioelectrical signal via one or more of electrodes 24, 26. Processing circuit 60 also receives sensor data from accelerometer 80 and sensor 74. As described above, in the techniques described in this disclosure, the sensed bioelectrical signal and the signal received from accelerometer 80 and sensor 74 are examples of sensor data. There may be additional examples of sensor data, such as other signals that are generated by the patient or are generated in response to behavior. In general, the sensor data that processing circuit 60 receives may be indicative of a patient condition (e.g., patient tremors).

Although three sensing sources are illustrated (e.g., sensing circuit 66, accelerometer 80, and sensor 74 are examples of hardware sensing sources), the techniques are not so limited. There may be fewer sensing sources, including a single sensing source, or there may be more sensing sources than those illustrated in FIG. 2.

Each of sensing circuit 66, accelerometer 80, and/or sensor 74 (e.g., each of the sensing sources) may store respective sensor data in memory 62 (e.g., via a direct connection to memory 62 and under control of processing circuit 60 or via telemetry circuit 70). In the example techniques described in this disclosure, processing circuit 60 may execute data pre-processor application 82. In response to executing application 82, processing circuit 60 may receive, possibly from memory 62, sample values of sensor data from one or more sensing sources. In this way, processing circuit 60 may receive sensor data from one or more sensing sources.

Processing circuit 60, via application 82, may determine whether each sample value from sensor data from respective sensing sources is valid or invalid. As one example, for sample values from each sensing source, there may be a predetermined range, stored in memory 62 or memory of processing circuit 60, and if values from the sensing source are within that range, the values are valid. If the values from the sensing source are outside that range, the values are invalid. Invalid data also refers to lost or dropped sample values (e.g., where a sample value is expected but none is received). Processing circuit 60 may compare each of the sample values from respective sensing sources to the respective predetermined ranges. If processing circuit 60 determines that the value is out-of-band (e.g., outside the valid range), processing circuit 60, via application 82, may identify the locations in the sensor data sample value stream where the sample value is invalid. Optionally, processing circuit 60 may identify the sensor data that is valid, or a combination of both.

Processing circuit 60 may store information identifying the sample values that are invalid or identifying the sample values that are valid, or both. In this way, processing circuit 60 may determine error locations in the received sensor data, where the error locations include invalid data. Processing circuit 60 may store information of the error locations, or more generally, the number of invalid sample values in memory 62 and/or local memory.

Although not necessary in all examples, processing circuit 60 may execute interpolation application 84. Processing circuit 60, via application 84, may generate replacement values for the invalid values. There may be various algorithms to interpolate. As one example, processing circuit 60, via application 84, may interpolate based on sensor data values (e.g., sample values) in non-error locations of the sensor data to generate interpolated data values. For instance, processing circuit 60 may interpolate sensor data values in the error locations based on sensor data values in non-error locations of the sensor data. The interpolations may be linear interpolation (e.g., average of sensor data value of immediately preceding non-error location relative to error location and sensor data value of immediately subsequent non-error location relative to error location) but other interpolation techniques may be possible. Processing circuit 60, via application 84, may identify which are the replacement values. In this way, processing circuit 60, via application 82 and application 84, may flag sample values as being either an observed data point (e.g., valid), an invalid data point, or, as applicable, an interpolated/extrapolated data point.

Processing circuit 60 may execute confidence level application 86. Processing circuit 60 may execute application 86 before, in parallel with, or after execution of application 84, in examples where processing circuit 60 executes interpolation application 84. Processing circuit 60, via application 86, may determine confidence levels for sensor data received from each of the plurality of sensing sources, where each of the confidence levels of the sensor data from each of the sensing sources is a measure of accuracy of the sensor data received from respective sensing sources.

As one example, processing circuit 60, via application 82, may have marked each error location in the sensor data (e.g., store information identifying the sample values that are invalid or identifying the sample values that are valid, or both). In such example, processing circuit 60, via application 86, may determine at least one of a number of error locations in the received sensor data or a number of interpolated sample values, where the error locations include invalid data. Processing circuit 60, via application 86, may determine the one or more confidence levels based on at least one of the determined number of error locations or the number of interpolated sample values. As another example, processing circuit 60, via application 82, may have determined a number of data packet losses in the received sensor data. The data packet may include measured sample values of sensore, but need not necessarily be sample values of sensor data. For instance, the data packets may be header information and like, and although not sensor data, loss of data packets may be indicative that the received sensor data is not accurate because the interconnection between sensor and IMD 16 may be poor. Processing circuit 60, via application 86, may determine the one or more confidence levels based on the number of data packets losses in the received sensor data.

For instance, processing circuit 60 may determine that 1% of data is invalid for a particular sensing source, and determine that the confidence level for the sensor data from that sensing source is 99%, determine that 2% of data is invalid for a particular sensing source, and determine that the confidence level for the sensor data from that sensing source is 98%, and so forth. As another example, processing circuit 60 may determine that if a particular percentage (e.g., 80%) of the data is valid for a particular sensing source, then the confidence level is a digital one (indicating confidence), and if less than the particular percentage (e.g., 80%) of the data is valid for a particular sensing source, then the confidence level is a digital zero (indicating no confidence). Processing circuit 60 may similarly use loss of data packets for determining confidence level.

Processing circuit 60 may execute therapy determination application 88 to determine one or more therapy parameter values based on one or more confidence levels. For instance, processing circuit 60 may store the confidence levels, as generated from the execution of application 86 in local memory or memory 62. Then, based on the confidence levels, processing circuit 60 may determine therapy parameter values (e.g., determine a therapy program from therapy programs 72 that corresponds to the determined therapy parameter values).

One way to determine the therapy parameter values is based on rules and control policies 76. Processing circuit 60, via application 88, may determine a plurality of available control policies in rules and control polices 76 based on the confidence levels. As described above, rules and control policies 76 may define a plurality of therapy parameter values. In some examples, the plurality of therapy parameter values defined by rules and control policies 76 may include a range of therapy parameter values, and rules and control policies 76 may define maximum and minimum therapy parameter values, and possibly a rate at which the therapy parameter values can be adjusted. In one example, processing circuit 60, via application 88, may determine a manner in which to ramp (e.g., ramp up or ramp down) the therapy parameter values of the therapy currently being delivered based on the plurality of available control policies.

For example, based on the plurality of available control policies, processing circuit 60 may determine that the amplitude can reach a maximum of a particular amplitude. Also, processing circuit 60 may utilize the received sensor data to determine what the amplitude of the therapy should be. As an example, if the received sensor data indicates that the therapy is not sufficiently addressing the disorder (e.g., an amplitude of the sensor data is greater than expected, or amplitude of the sensor data is less than expected), then processing circuit 60, via application 88, may determine what the amplitude, pulse width, frequency, and/or other parameter value. for the therapy should be such that the received sensor data indicates that the therapy is sufficiently addressing the disorder.

Processing circuit 60 may then ramp the amplitude of the therapy based on the determination of what the therapy parameter values of the therapy should be and the maximum or minimum values for the therapy parameter values. In this example, if the confidence level of the sensor data that processing circuit 60 uses to determine that the amplitude should be increased is relatively low, then the available control policies may be such that the maximum allowable amplitude (e.g., selectable by a user or clinician) is limited to be less than a maximum amplitude. In this case, even if the processing circuit 60 determines that the amplitude of the therapy should be greater than the maximum allowable amplitude (e.g., based on the sensor data which may not be sufficiently accurate), the actual amplitude may be limited by the available control policies to be no more than the maximum allowable amplitude.

In some examples, in determining which control policies of rules and control polices 76 are available, processing circuit 60, via application 88, may weigh one or more of the confidence levels differently. For example, the sensor data from a first sensing source may be a better indicator of the therapy as compared to sensor data from a second sensing source. In this example, if the confidence level of the sensor data from the first sensing source is lower than the confidence level of the senor data from the second sensing source, then IMD 16 may further limit the available control policies, as compared to the case where the confidence level of the sensor data from the second sensing source is lower than the confidence level of the sensor data from the first sensing source. Accordingly, processing circuit 60, via application 88, may weigh the confidence level of the sensor data from the first sensor more heavily than the confidence level of the sensor data from the second sensor in determining the available control policies. Here, weighing more heavily means that the confidence level of the sensor data from the first sensor has a greater effect in determining which control policies are available as compared to the confidence level of the sensor data from the second sensor.

Processing circuit 60, via therapy determination application 88, may use the confidence levels to determine which control policies in rules and control policies 76 are available. In this disclosure, the confidence level used to determine which control policies are available is used to encompass both the examples where non-weighted confidence levels are used and examples where weighted confidence levels are used.

To determine which control policies in rules and control policies 76 are available, processing circuit 60, via application 88, may repeatedly determine whether the one or more confidence levels are compliant with one or more conditions of the plurality of rules in rules and control policies 76 until the one or more confidence levels are compliant with one or more conditions of a rule of the plurality of rules (e.g., until condition or conditions of a rule are satisfied). Processing circuit 60, via application 88, may determine a set of available therapy parameter values associated with a rule. For example, processing circuit 60, via application 88, may determine which control policies are associated with the rule, and determine which set of therapy parameter values define the available control policies. In this example, processing circuit 60, via application 88, may determine one or more therapy parameter values based on the determined set of available therapy parameter values.

As an example, processing circuit 60, via therapy determination application 88, may determine whether the confidence levels are compliant with conditions of a first rule that is associated with a set of available therapy parameter values. Processing circuit 60, via therapy determination application 88, may determine the one or more therapy parameter values based on the set of available therapy parameter for the first rule.

However, processing circuit 60, via therapy determination application 88, may determine that the confidence levels are not compliant with the conditions of the first rule. In this case, subsequent to determining that the one or more confidence levels are not compliant with the conditions of the first rule, processing circuit 60, via therapy determination application 88, may determine that the confidence levels are compliant with the conditions of a second rule. In this example, processing circuit, via therapy determination application 88, may determine the therapy parameter values based on the set of available therapy parameter values associated with the second rule.

In some cases, processing circuit 60, via therapy determination application 88, may determine that the confidence levels are not compliant with conditions of any of the rules. In such examples, in response to determining that the confidence levels are not compliant with conditions of the rules, processing circuit 60, via therapy determination application 88, may determine that conditions associated with using a set of default therapy parameter values are met. In general, the conditions associated with the set of default therapy parameter values should be selected such that the conditions are always met if the conditions for all other rules are not met. Processing circuit 60, via therapy determination application 88, may determine the therapy parameter values based on the set of default therapy parameter values in response to the conditions associated with using the set of default therapy parameter values being met.

In this way, processing circuit 60 may determine the therapy parameter values for the therapy that is to be delivered. In some examples, processing circuit 60 may identify a therapy program from therapy programs 72 that includes therapy parameter values closest to those of the determined therapy parameter values, or may generate a new therapy program that includes the determined therapy parameter values. Processing circuit 60 may then cause signal generator circuit 64 to deliver therapy based on the determined one or more therapy parameter values.

Accordingly, processing circuit 60 may utilize data-signal-specific validation criteria (e.g., evaluating the confidence levels against the conditions of the rules) that indicates whether the invalid sample values or interpolated/extrapolated sample values within a current time range is small enough (e.g., the number of errors in small enough) for the sensor data to be considered valid for determining therapy, or too speculative (not sufficiently reliable because there are too many errors) to be utilized. For instance, the conditions of a rule may never be satisfied (e.g., a rule can never be considered true) when sensor data involved in evaluating the rule is considered too speculative to use. The sensor data may be considered too speculative, for example, if the confidence level of the sensor data is below a threshold, indicating that the sensor data therefore should not be used for determining therapy parameter values.

Telemetry circuit 70 is configured to support wireless communication between IMD 16 and an external device 14, sensor 74, or another computing device. Processing circuit 60 of IMD 16 may receive, as updates to programs, values for various stimulation parameters such as amplitude and electrode combination, from device 14 via telemetry circuit 70. The updates to the therapy programs may be stored within therapy programs 72 of memory 62. Telemetry circuit 70 in IMD 16, as well as telemetry circuits in other devices and systems described herein, such as device 14, may accomplish communication by RF communication techniques. In addition, telemetry circuit 70 may communicate with external device 14 via proximal inductive interaction of IMD 16 with device 14. Accordingly, telemetry circuit 70 may send information to device 14 on a continuous basis, at periodic intervals, or upon request from IMD 16 or device 14. For example, processing circuit 60 may transmit brain state information to device 14 via telemetry circuit 70.

Although not illustrated, IMD 16 includes a power source that delivers operating power to various components of IMD 16. The power source may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

FIG. 3 is a conceptual diagram illustrating hierarchy of therapy programs and associated rules. For instance, FIG. 3 illustrates an example data structure for rules and control policies 76 that memory 62 may store. For each rule, there may be associated one or more conditions, which may be considered as a Boolean combination of predicates that, when true, indicate which therapy parameter values are available.

Processing circuit 60 may determine whether the confidence levels are compliant with the conditions of a first rule. A first rule may include the conditions that confidence levels of sensor data from sensing sources is greater than 80%. If the Boolean condition that all confidence levels from all sensor sources are greater than 80% is true, then processing circuit 60 may select from any of the control policies from A1-D4.

If processing circuit 60 determines that the confidence levels are not compliant with the conditions of the first rule, processing circuit 60 determines whether the confidence rules are compliant with the conditions of a second rule. In FIG. 3, a second rule may include the conditions that the confidence levels of sensor data from first and second sensing sources is greater than 80%, and a confidence level from a third sensing source is less than 80%. If the Boolean AND combination of the conditions of the second rule are true (i.e., confidence levels of sensor data from first and second sensing sources is greater than 80% AND a confidence level from a third sensing source is less than 80%), then processing circuit 60 may select from the control policies from A1, A2, A3, B1, B2, B3, C1, and C2. In this example, the control policies for the second rule are a subset of the control policies of the first rule. In general, the therapy parameter values for a second rule associated with control policies that are lower in the hierarchical layers of control policies may be a subset of therapy parameter values for a first rule associated with control policies that are higher in the hierarchical layers.

In the example illustrated in FIG. 3, if the confidence levels for all sensing sources is less than 20%, then only control policies A1, B1, and A2 may be available. In this example, A1, B1, and A2 represent default parameters. Processing circuit 60 may determine that A1, B1, and A2 are the only available control policies based on the confidence levels being below a minimum confidence threshold level (e.g., 20% in this example).

Figure 4:
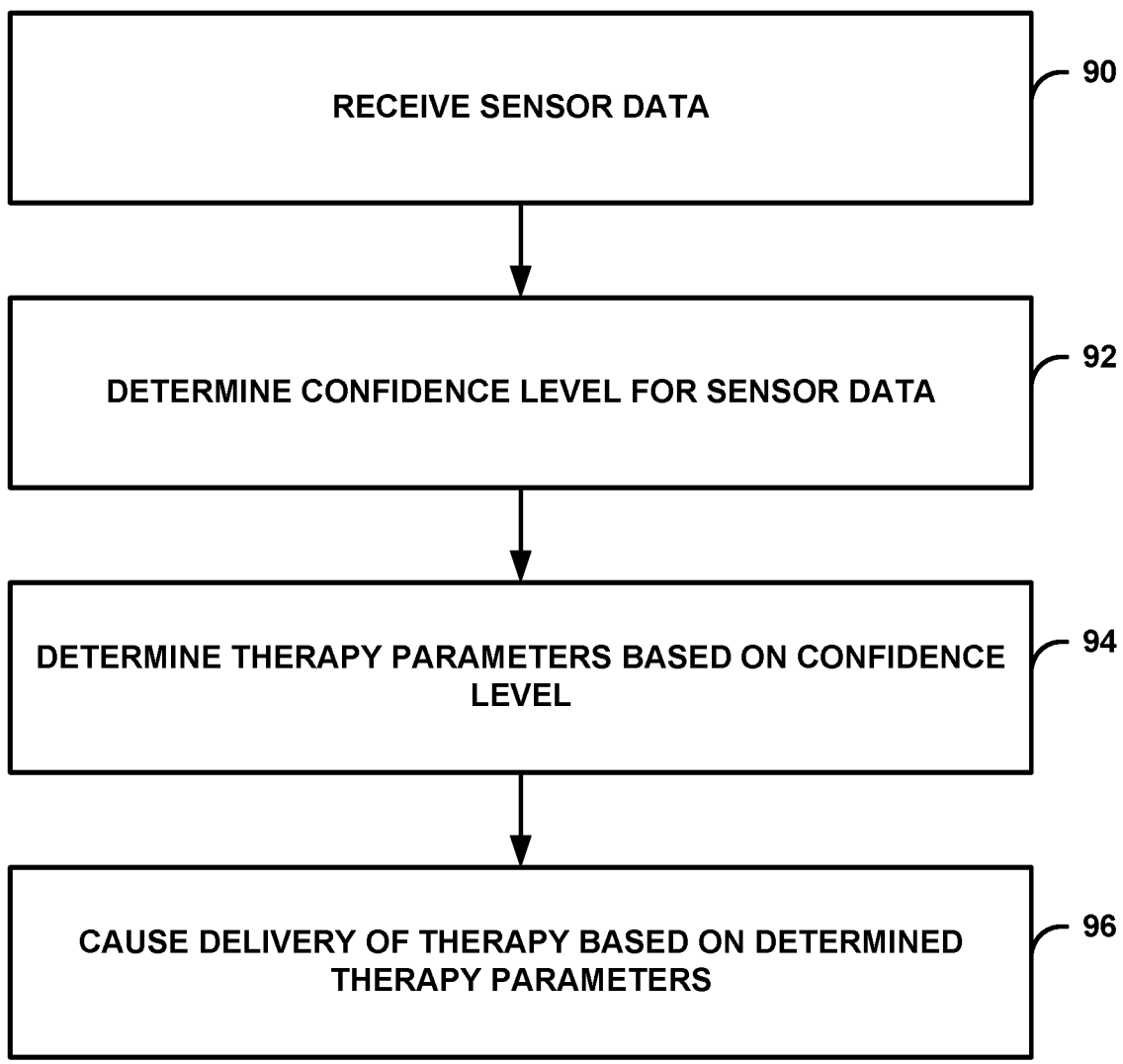
FIG. 4 is a flow diagram illustrating an example technique for therapy adjustment in response to loss of sensor data in accordance with one or more aspects of this disclosure.

FIG. 4 is a flow diagram illustrating an example technique in accordance with one or more aspects of this disclosure. Processing circuit 60 may receive sensor data generated by one or more hardware sensing sources (90). As an example, each of the sensing sources may store the sensor data generated by respective sensing sources in memory 62 or some other storage location. Processing circuit 60 may execute data pre-processor application 82 to retrieve the stored sensor data.

In addition, processing circuit 60, via application 82, may identify which sample values for the sensor data are invalid and/or valid. In some examples, processing circuit 60 may execute interpolation application 84 to generate interpolated values that fill in for the invalid data. Processing circuit 60, via application 84, may identify sample values that were interpolated/extrapolated.

Processing circuit 60 may determine one or more confidence levels for sensor data generated by each of the plurality of sensing sources, where each of the confidence levels of the sensor data from each of the sensing sources is a measure of accuracy of the sensor data received from respective sensing sources (92). As one example, processing circuit 60 may execute confidence level application 86 to determine a number of invalid values or interpolated/extrapolated values, and determine the confidence level based on the number of invalid or interpolated/extrapolated values. As another example, processing circuit 60 may execute confidence level application 86 to determine a number of data packet losses, and determine the confidence level based on the number of data packet losses.

With the execution of therapy determination application 88, processing circuit 60 may determine one or more therapy parameter values based on the determined confidence levels (94). In addition to the confidence levels, processing circuit 60, via application 88, may utilize the sample values (e.g., interpolated and actual values) to determine the therapy parameter values. As an example, application 88 may cause processing circuit 60 to determine available control policies based on the confidence levels, and determine a manner in which to ramp (e.g., ramp up or ramp down) therapy parameter values based on the available control policies and the sensor data.

In general, application 88 may cause processing circuit 60 to repeatedly determine whether the confidence levels are compliant with conditions of rules until the confidence levels are compliant with conditions of a rule. Processing circuit 60 may determine a set of available therapy parameter values associated with the rule, and determine the one or more therapy parameter values based on the determined set of available therapy parameter values.

For instance, processing circuit 60 may determine that the confidence levels are compliant with conditions of a rule, where the rule is associated with a set of available therapy parameter values. Processing circuit 60 may determine the one or more therapy parameter values based on the set of available therapy parameter values.

However, in some cases, processing circuit 60 may determine that the confidence levels are not compliant with conditions of a first rule, where the first rule is associated with a first set of available therapy parameter values, and subsequent to determining that the confidence levels are not compliant with the conditions of the first rule, determine that the confidence levels are compliant with conditions of a second rule, where the second rule is associated with a second set of available therapy parameter values. In this example, processing circuit 60 may determine the one or more therapy parameter values based on the second set of available therapy parameter values. The second set of available therapy parameter values may be a subset of the first set of available therapy parameter values.

In some cases, processing circuit 60 may determine that the confidence levels are not compliant with conditions of one or more rules, and in response to determining that the confidence levels are not compliant with conditions of one or more rules, determine that conditions associated with using a set of default therapy parameter values are met. In such cases, processing circuit 60 may determine the one or more therapy parameter values based on the set of default therapy parameter values in response to the conditions associated with using the set of default therapy parameter values being met. Processing circuit 60 may determine the one or more therapy parameter values based on the set of default therapy parameter values in response to the confidence levels being below a minimum confidence threshold level.

Processing circuit 60 may use the actual the confidence levels to determine the one or more therapy parameter values, but the example techniques are not so limited. In some examples, processing circuit 60 weigh one or more of the confidence levels (e.g., assign different weights to the confidence levels). Processing circuit 60 may then determine the therapy parameter value(s) based on the weighted confidence levels.

As an example, sensor data from a first sensor may be more useful in determining therapy parameter values as compared to sensor data from a second sensor. In such an example, if the sensor data from the first sensor is accurate (e.g., high confidence level), then even if the sensor data from the second sensor is not very accurate (e.g., low confidence level), processing circuit 60 may not need to adjust the therapy parameter values. However, if the sensor data form the first sensor is not very accurate, and the sensor data from the second sensor is accurate, processing circuit 60 may substantially adjust the therapy parameter values. Accordingly, the effect of sensor data from different sensors on the therapy parameters may not all be the same.

To account for the different importance of the sensor data, processing circuit 60 may weigh the confidence levels. For example, processing circuit 60 may assign a higher weight to confidence level for the first sensor than the weight to the confidence level for the second sensor. Processing circuit 60 may then average the weighted confidence levels to determine an average weighted confidence level that processing circuit 60 uses to determine the therapy parameter values. By weighting, the confidence level of the sensor data that has greater effect on the determination of the therapy parameters may drive the determination of the therapy parameter values. In this disclosure, determining therapy parameter values based on the confidence levels includes both the example where weighting is used and the example where weighting is not used.

Processing circuit 60 may cause delivery of therapy based on the determined therapy parameter values (96). For instance, processing circuit 60 may control signal generator circuit 64 to deliver therapy based on the determined therapy parameter values. As an example, processing circuit 60 may cause signal generator circuit 64 to ramp the one or more therapy parameter values in the manner determined from the available control policies.

In this manner, the example techniques may promote ways in which to ensure the proper therapy is delivered even in instances where there is sensor data loss or dropout. For example, IMD 16 may be operating correctly and delivering therapy based on measurements from one or more sensors, but due to patient movement or adjustment or damage to a sensor, there may be dropout of the sensor data from one or more of the sensors. The example techniques may address this potential issue by implementing an algorithm of determining the confidence of the received sensor data. If there is high confidence in the received sensor data, then IMD 16 may continue operating normally. However, if there is low confidence in the received sensor data, then IMD 16 may re-determine the therapy parameter values to provide effective therapy and minimize unintended results.

Figure 5:
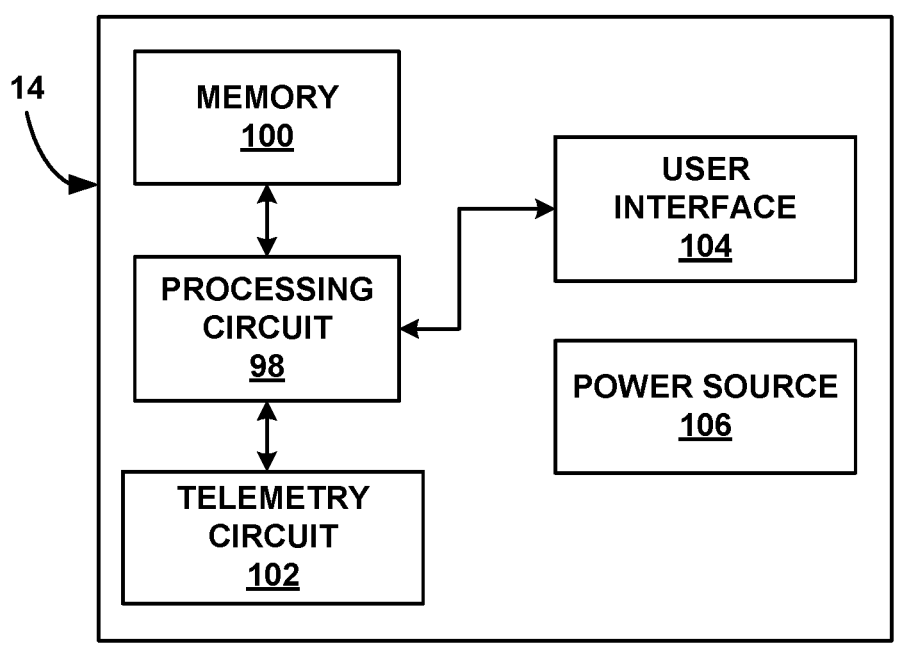
FIG. 5 is a functional block diagram illustrating components of an example external device that may communicate with the medical device of FIG. 2.

FIG. 5 is a functional block diagram illustrating components of an example external device 14. External device 14 may operate as a patient programmer or clinician programmer configured to permit a user to program and/or control therapy parameter values of IMD 16. External device 14 includes processing circuit 98, memory 100, telemetry circuit 102, user interface 104, and power source 106. Processing circuit 98 controls user interface 104 and telemetry circuit 102, and stores and retrieves information and instructions to and from memory 100. Device 14 may be configured for use as a clinician programmer or a patient programmer. Processing circuit 98 may comprise any combination of one or more processors including one or more microprocessors, DSPs, ASICs, FPGAs, or other equivalent integrated or discrete logic circuitry. Accordingly, processing circuit 98 may include any suitable structure, whether in hardware, software, firmware, or any combination thereof, to perform the functions ascribed herein to processing circuit 98.

A user, such as a clinician or patient 12, may interact with device 14 through user interface 104. User interface 104 includes a display (not shown), such as a LCD or LED display or other type of screen, with which processing circuit 98 may present information related to the therapy. In addition, user interface 104 may include an input mechanism to receive input from the user. The input mechanisms may include, for example, buttons, a keypad (e.g., an alphanumeric keypad), a peripheral pointing device or another input mechanism that allows the user to navigate through user interfaces presented by processing circuit 98 of device 14 and provide input.

If device 14 includes buttons and a keypad, the buttons may be dedicated to performing a certain function (i.e., a power button), or the buttons and the keypad may be soft keys that change function depending upon the section of the user interface currently viewed by the user. In addition, or instead, the screen (not shown) of programmer 14 may be a touch screen that allows the user to provide input directly to the user interface shown on the display. The user may use a stylus or their finger to provide input to the display. In other examples, user interface 104 also includes audio circuitry for providing audible notifications, instructions or other sounds to patient 12, receiving voice commands from patient 12, which may be useful if patient 12 has limited motor functions, or both. Patient 12, a clinician or another user may also interact with device 14 to manually select therapy programs, generate new therapy programs, modify therapy programs through individual or global adjustments, and transmit the new programs to IMD 16.

In some examples, at least some of the control of therapy delivery by IMD 16 may be implemented by processing circuit 98 of device 14. For instance, the example techniques described above with respect to processing circuit 60 of IMD 16 may be implemented in other examples, at least in part, by processing circuit 98, or the combination of processing circuit 60 and processing circuit 98 may perform the example techniques. As one example, processing circuit 98 may receive sensor data that telemetry circuit 70 outputs to telemetry circuit 102. Processing circuit 98 may determine confidence levels, and determine therapy parameter values based on the confidence levels. Processing circuit 98 may then cause IMD 16 to deliver therapy based on the determined therapy parameter values.

Memory 100 may include instructions for operating user interface 104 and telemetry circuit 102, and for managing power source 106. In some examples, memory 100 may also store any therapy data retrieved from IMD 16 during the course of therapy, biomarker information, sensed bioelectrical brain signals, and the like. In some instances, the clinician may use this therapy data to determine the progression of the patient condition in order to plan future treatment for the movement disorder (or other patient condition) of patient 12. Memory 100 may include any volatile or nonvolatile memory, such as RAM, ROM, EEPROM or flash memory. Memory 100 may also include a removable memory portion that may be used to provide memory updates or increases in memory capacities. A removable memory may also allow sensitive patient data to be removed before device 14 is used by a different patient.

Wireless telemetry in device 14 may be accomplished by RF communication or proximal inductive interaction of external device 14 with IMD 16. This wireless communication is possible through the use of telemetry circuit 102. Accordingly, telemetry circuit 102 may be similar to the telemetry circuit contained within IMD 16. In other examples, device 14 may be capable of infrared communication or direct communication through a wired connection. In this manner, other external devices may be capable of communicating with device 14 without needing to establish a secure wireless connection.

Power source 106 is configured to deliver operating power to the components of device 14. Power source 106 may include a battery and a power generation circuit to produce the operating power. In some examples, the battery may be rechargeable to allow extended operation. Recharging may be accomplished by electrically coupling power source 106 to a cradle or plug that is connected to an alternating current (AC) outlet. In addition, recharging may be accomplished through proximal inductive interaction between an external charger and an inductive charging coil within device 14. In other examples, traditional batteries (e.g., nickel cadmium or lithium ion batteries) may be used. In addition, device 14 may be directly coupled to an alternating current outlet to operate.

While the techniques described above are primarily described as being performed by processing circuit 60 of IMD 16, in other examples, one or more other circuits may perform any part of the techniques described herein alone or in addition to processor 60. Thus, reference to "a processing circuit" may refer to "one or more processing circuits." Likewise, "one or more processing circuits" may refer to a single processing circuit or multiple processing circuits in different examples.

The techniques described in this disclosure, including those attributed to IMD 16, external device 14, or various constituent components, may be implemented, at least in part, in hardware, software, firmware or any combination thereof. For example, various aspects of the techniques may be implemented within one or more processing circuits, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor" or "processing circuit" as used herein may refer to one or more of any of the foregoing structure or any other structure suitable for implementation of the techniques described herein.

It will be understood that the techniques described in this disclosure may be utilized to deliver therapy to a patient to treat a variety of symptoms or patient conditions such as chronic pain, Parkinson's disease, other types of movement disorders, seizure disorders (e.g., epilepsy), urinary or fecal incontinence, sexual dysfunction, obesity, mood disorders (e.g., depression), gastroparesis or diabetes. Additionally, while the patient signal indicative of a patient condition may be based on patient movement as sensed by an accelerometer or gyroscope, the patient signal could alternatively or additionally be other physiological signals.

In addition, in some aspects, the functionality described herein may be provided within dedicated hardware and/or software executing on hardware. Depiction of different features is intended to highlight different functional aspects and does not necessarily imply that such features must be realized by separate hardware or software components. Rather, the functionality may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external device, a combination of an IMD and external device, an integrated circuit (IC) or a set of ICs, and/or discrete electrical circuitry, residing in an IMD and/or external device.

Various examples have been described. These and other examples are within the scope of the following claims.

What is claimed is:

1. A method of therapy delivery, the method comprising:
    receiving sensor data generated by plurality of hardware sensing sources;
    determining a control policy to utilize for determining one or more therapy parameter values based on the received sensor data, wherein the control policy is one of a plurality of control policies in a hierarchical arrangement, and each of the control policies is associated with a respective set of one or more conditions and respective one or more therapy parameter values;
    determining one or more therapy parameter values based on the respective one or more therapy parameter values associated with the determined control policy; and
    causing delivery of therapy based on the determined one or more therapy parameter values.

2. The method of claim 1, wherein determining the control policy comprises determining that the respective set of one or more conditions associated with the control policy are satisfied.

3. The method of claim 1, wherein determining the one or more therapy parameters values comprises determining a manner in which to ramp the one or more therapy parameter values based on the determined control policy, and wherein causing delivery of therapy comprises ramping the one or more therapy parameter values in the determined manner.

4. The method of claim 1, wherein the control policy is a first control policy of the plurality of control policies that is associated with a first set of one or more therapy parameter values, wherein the plurality of control policies includes a second control policy that is associated with a second set of one or more therapy parameter values, wherein the second set of one or more therapy parameter values are a subset of the first set of one or more therapy parameter values, and wherein the first control policy is higher in the hierarchical arrangement than the second control policy.

5. The method of claim 1, wherein the control policy comprises a first control policy, and the plurality of control policies comprises the first control policy and a second control policy, the method further comprising:
    determining that the respective set of one or more conditions associated with the second control policy are not satisfied; and
    in response to determining that the respective set of one or more conditions associated with the second control policy are not satisfied, determining whether the respective set of one or more conditions associated with the first control policy are satisfied,
    wherein determining the control policy comprises determining the control policy based on the respective set of one or more conditions associated with the first control policy being satisfied,
    wherein the second control policy is higher in the hierarchical arrangement than the first control policy, and
    wherein the determination that the respective set of one or more conditions associated with the second control policy are not satisfied occurs before the determination of whether the respective set of one or more conditions associated with the first control policy are satisfied based on the second control policy being higher in the hierarchical arrangement than the first control policy.

6. The method of claim 1, wherein the plurality of control policies comprise a default set of control policies that define a default set of one or more therapy parameter values, wherein the default set of one or more therapy parameter values are determined when respective sets of one or more conditions associated with other control policies are not satisfied.

7. The method of claim 1, further comprising:
    determining confidence levels for sensor data generated by each of the plurality of sensing sources,
    wherein determining the control policy to utilize comprises determining the control policy based on the determined confidence levels satisfying the respective set of one or more conditions associated with the control policy.

8. The method of claim 1, wherein the therapy comprises electrical stimulation therapy and the one or more therapy parameter values comprise one or more of amplitude, frequency, and pulse width.

9. The method of claim 1, wherein the therapy is one of deep brain stimulation (DBS), spinal cord stimulation (SCS), or pelvic stimulation.

10. The method of claim 1, wherein determining the control policy comprises:
    evaluating respective set of one or more conditions of the plurality of policies in order of the hierarchical arrangement until the respective set of one or more conditions of one of the control policies is satisfied,
    wherein the control policy comprises the first control policy evaluated in the hierarchical arrangement for which the one or more conditions are satisfied.

11. A medical system for therapy delivery, the medical system comprising:
    a plurality of hardware sensing sources configured to generate sensor data; and
    a processing circuit configured to:
        receive sensor data generated by plurality of hardware sensing sources;
        determine a control policy to utilize for determining one or more therapy parameter values based on the received sensor data, wherein the control policy is one of a plurality of control policies in a hierarchical arrangement, and each of the control policies is associated with a respective set of one or more conditions and respective one or more therapy parameter values;

determine one or more therapy parameter values based on the respective one or more therapy parameter values associated with the determined control policy; and cause delivery of therapy based on the determined one or more therapy parameter values.

12. The medical system of claim 11, further comprising an implantable medical device (IMD), wherein the IMD comprises the plurality of hardware sensing sources and the processing circuit.

13. The medical system of claim 11, wherein to determine the control policy, the processing circuit is configured to determine that the respective set of one or more conditions associated with the control policy are satisfied.

14. The medical system of claim 11, wherein to determine the one or more therapy parameters values, the processing circuit is configured to determine a manner in which to ramp the one or more therapy parameter values based on the determined control policy, and wherein to cause delivery of therapy, the processing circuit is configured to ramp the one or more therapy parameter values in the determined manner.

15. The medical system of claim 11, wherein the control policy is a first control policy of the plurality of control policies that is associated with a first set of one or more therapy parameter values, wherein the plurality of control policies includes a second control policy that is associated with a second set of one or more therapy parameter values, wherein the second set of one or more therapy parameter values are a subset of the first set of one or more therapy parameter values, and wherein the first control policy is higher in the hierarchical arrangement than the second control policy.

16. The medical system of claim 11, wherein the control policy comprises a first control policy, and the plurality of control policies comprises the first control policy and a second control policy, and wherein the processing circuit is configured to:

determine that the respective set of one or more conditions associated with the second control policy are not satisfied; and in response to determining that the respective set of one or more conditions associated with the second control policy are not satisfied, determine whether the respective set of one or more conditions associated with the first control policy are satisfied, wherein to determine the control policy, the processing circuit is configured to determine the control policy based on the respective set of one or more conditions associated with the first control policy being satisfied, wherein the second control policy is higher in the hierarchical arrangement than the first control policy, and wherein the determination that the respective set of one or more conditions associated with the second control policy are not satisfied occurs before the determination of whether the respective set of one or more conditions associated with the first control policy are satisfied based on the second control policy being higher in the hierarchical arrangement than the first control policy.

17. The medical system of claim 11, wherein the plurality of control policies comprise a default set of control policies that define a default set of one or more therapy parameter values, wherein the default set of one or more therapy parameter values are determined when respective sets of one or more conditions associated with other control policies are not satisfied.

18. The medical system of claim 11, wherein the therapy comprises electrical stimulation therapy and the one or more therapy parameter values comprise one or more of amplitude, frequency, and pulse width.

19. The medical system of claim 11, wherein the therapy is one of deep brain stimulation (DBS), spinal cord stimulation (SCS), or pelvic stimulation.

20. The medical system of claim 11, wherein to determining the control policy, the processing circuit is configured to:

evaluate respective set of one or more conditions of the plurality of policies in order of the hierarchical arrangement until the respective set of one or more conditions of one of the control policies is satisfied, wherein the control policy comprises the first control policy evaluated in the hierarchical arrangement for which the one or more conditions are satisfied.

21. The medical system of claim 11, further comprising a stimulation generator configured to deliver the therapy based on the determined one or more therapy parameter values.

22. A computer-readable storage medium storing instructions thereon that when executed cause one or more processors to:

receive sensor data generated by plurality of hardware sensing sources;

determine a control policy to utilize for determining one or more therapy parameter values based on the received sensor data, wherein the control policy is one of a plurality of control policies in a hierarchical arrangement, and each of the control policies is associated with a respective set of one or more conditions and respective one or more therapy parameter values;

determine one or more therapy parameter values based on the respective one or more therapy parameter values associated with the determined control policy; and cause delivery of therapy based on the determined one or more therapy parameter values.

23. The computer-readable storage medium of claim 22, wherein the instructions that cause the one or more processors to determine the control policy comprise instructions that cause the one or more processors to determine that the respective set of one or more conditions associated with the control policy are satisfied.

24. The computer-readable storage medium of claim 22, wherein the instructions that cause the one or more processors to determine the one or more therapy parameters values comprise instructions that cause the one or more processors to determine a manner in which to ramp the one or more therapy parameter values based on the determined control policy, and wherein the instructions that cause the one or more processors to cause delivery of therapy comprise instructions that cause the one or more processors to ramp the one or more therapy parameter values in the determined manner.

25. The computer-readable storage medium of claim 22, wherein the control policy is a first control policy of the plurality of control policies that is associated with a first set of one or more therapy parameter values, wherein the plurality of control policies includes a second control policy that is associated with a second set of one or more therapy parameter values, wherein the second set of one or more therapy parameter values are a subset of the first set of one or more therapy parameter values, and wherein the first control policy is higher in the hierarchical arrangement than the second control policy.

26. The computer-readable storage medium of claim 22, wherein the control policy comprises a first control policy, and the plurality of control policies comprises the first control policy and a second control policy, and the instructions further comprise instructions that cause the one or more processors to:
   determine that the respective set of one or more conditions associated with the second control policy are not satisfied; and
   in response to determining that the respective set of one or more conditions associated with the second control policy are not satisfied, determine whether the respective set of one or more conditions associated with the first control policy are satisfied,
   wherein the instructions that cause the one or more processors to determine the control policy comprise instructions that cause the one or more processors to determine the control policy based on the respective set of one or more conditions associated with the first control policy being satisfied,
   wherein the second control policy is higher in the hierarchical arrangement than the first control policy, and
   wherein the determination that the respective set of one or more conditions associated with the second control policy are not satisfied occurs before the determination of whether the respective set of one or more conditions associated with the first control policy are satisfied based on the second control policy being higher in the hierarchical arrangement than the first control policy.

* * * * *